(12) United States Patent
Jiang et al.

(10) Patent No.: US 8,728,015 B2
(45) Date of Patent: May 20, 2014

(54) ELECTRONICALLY CONTROLLED WIDE BAND VIBRATING TAMPON WITH LOW DISPOSABLE COST

(75) Inventors: Xu Hua Jiang, San Jose, CA (US); Min Lu, San Jose, CA (US)

(73) Assignee: Lustone Technology, Inc., San Jose, CA (US)

( * ) Notice: Subject to any disclaimer, the term of this patent is extended or adjusted under 35 U.S.C. 154(b) by 768 days.

(21) Appl. No.: 12/978,584

(22) Filed: Dec. 26, 2010

(65) Prior Publication Data

US 2012/0089056 A1    Apr. 12, 2012

Related U.S. Application Data

(60) Provisional application No. 61/392,003, filed on Oct. 11, 2010.

(51) Int. Cl.
   *A61H 19/00*    (2006.01)
(52) U.S. Cl.
   USPC ............ 601/78; 601/46; 601/57; 601/84; 604/904
(58) Field of Classification Search
   USPC .......... 601/46, 48, 56, 57, 67, 69, 70, 78, 84, 601/87, 89, 92, 93, 134, DIG. 16; 604/385.01, 385.17, 904
   See application file for complete search history.

(56) References Cited

U.S. PATENT DOCUMENTS

| | | | |
|---|---|---|---|
| 6,183,428 B1* | 2/2001 | Kilgore | 601/70 |
| 8,535,286 B2* | 9/2013 | Conroy | 601/43 |
| 2010/0056963 A1* | 3/2010 | Shaviv | 601/46 |
| 2013/0060174 A1* | 3/2013 | Rolli et al. | 601/46 |

* cited by examiner

*Primary Examiner* — Quang D Thanh
(74) *Attorney, Agent, or Firm* — Chein-Hwa Tsao; CH Emily LLC

(57) ABSTRACT

The present invention is an electronically controlled wide band vibrating tampon (ECWVT) apparatus to provide relief from feminine menstrual cramps and comprises a controllable vibration generator with selectable wide band vibration sources, an electromechanical transducer aka a vibration transmitter, and a disposable vibration transmitting tampon head (VTTH) to be inserted into the user's vaginal canal for customized and maximized relief from a user's menstrual cramps. Since only the VTTH is disposable and all other parts are reusable, the disposable cost is minimized.

1 Claim, 13 Drawing Sheets

Fig. 1. Present Invention

Fig. 2. Present Invention

Fig. 3. Present Invention

Fig. 4. Present Invention

Fig. 5. Present Invention

Fig. 6. Present Invention

Fig. 7. Present Invention

Fig. 8. Present Invention

Fig. 9. Present Invention

Fig. 10. Present Invention

ELECTRONICALLY CONTROLLED WIDE BAND VIBRATING TAMPON WITH LOW DISPOSABLE COST

CROSS REFERENCE TO RELATED APPLICATIONS

This application is based upon and claims the priority of a previously filed provisional patent application entitled "Electronically. Controlled Wide Band Vibrating Tampon with Low Disposable Cost" by Jiang et al with application No. 61/392,003, filing date Oct. 11, 2010 whose content is herein incorporated by reference for all purposes.

FIELD OF INVENTION

The present invention relates generally to the field of sanitary tampon constructions. More specifically, the present invention is directed to techniques and associated device structures capable of generating controlled wide band variable vibration with low disposable cost.

BACKGROUND OF THE INVENTION

One method of trying to relieve the pain from cramps that a woman suffers during menstruation is to directly stimulate the walls of the vaginal canal. Typically, this stimulation is achieved by constructing a disposable sanitary tampon that includes a vibration mechanism. Prior art techniques have also included a power source and some control for the vibration mechanism that is located external to the tampon apparatus.

FIG. 11 illustrates a first prior art, disclosed in U.S. Pat. No. 5,782,779 by Kilgore, of a vibrating tampon apparatus 10 for easing a woman's menstrual cramps wherein the apparatus 10 includes an inner vibrator unit 12 and an outer tampon unit 11 surrounding the vibrator unit 12 which includes a vibrator motor 36 which is actuated by a tampon string 25 for imparting vibratory motion to the apparatus 10.

FIG. 12 illustrates a second prior art, disclosed in U.S. Pat. No. 6,183,428 by Kilgore, of an improved vibrating tampon apparatus 10 for easing a woman's menstrual cramps. The apparatus 10 includes an inner vibrator unit 12 and an outer tampon unit 11 dimensioned to be received in a woman's vaginal canal, and a remote power supply unit 13 disposed outside of the vaginal canal and operatively connected to the inner vibrator unit 12 for the purpose of preventing electrical shocks to the walls of the vaginal canal.

FIG. 13 illustrates a third prior art, disclosed in US patent application publication No. US 2007/0260210 A1 by Conroy, of another improved vibrating tampon apparatus 10 to provide relief from feminine menstrual cramps including a vibration element 20, a housing unit 14, and a tampon member 12. The vibration element 20 provides a source of vibrations and is contained within the housing unit 14. The tampon member 12 is fabricated of an absorbent material and covers at least a portion of the housing unit 14, while being held in place by retaining elements on the exterior of the housing unit 14. Electric power is supplied to the vibration element 20 by a remote electric power source, via a cable 16. The electrical connection between the electric power source and the vibration element 20 is controlled remotely by a control unit 18 that allows the apparatus to operate either momentarily, in a testing situation, or continually for the lifetime of the electric power source, which is for normal usage and cannot be interrupted by the user.

However, regardless of these prior arts just described there remains a need for the ability to have more controls of the vibration parameters for maximizing relief of user's feminine menstrual cramps and maximizing user's comfort. Furthermore, there also remains a need to reduce the disposable cost as the disposables are consumed regularly on an ongoing basis.

SUMMARY OF THE INVENTION

Under a variety of embodiments, the present invention is an electronically controlled wide band vibrating tampon (ECWVT) apparatus to provide relief from feminine menstrual cramps and it has a controllable vibration generator with selectable wide band vibration signal sources, a vibration transmitter, and a disposable vibration transmitting tampon head (VTTH) to be inserted into a user's vaginal canal for relief of a user's menstrual cramps. Since only the VTTH is disposable while all other parts are reusable, the disposable cost of the ECWVT is minimized.

In a more specific embodiment, the ECWVT includes a remote electronic controller (REC) for generating a variable wide band power electrical signal, an electromechanical transducer (EMT) electrically coupled to the REC for generating a mechanical vibration corresponding to the power electrical signal, and a handled housing (HDH) for enclosing and affixing the REC and the EMT.

In a specific embodiment, the REC includes a user interface, a central signal generating (CSG) device coupled to the user interface for generating a wide band electrical signal under the control of the user interface, and a power amplifier coupled to the CSG device for amplifying the wide band electrical signal into the power electrical signal.

In a more specific embodiment, the user interface includes a power on/off switch and numerous indicators, buttons, keys for increasing or decreasing signal frequency, changing signal waveform, and adjusting signal power level of the wide band power electrical signal.

In a more specific embodiment, the user interface further includes numerous external signal input ports for selectively passing along various external source signals into the wide band electrical signal and a corresponding signal selector.

In a more specific embodiment, the external signal input ports are configured to receive power signals such as white noise, pink noise, color noise, and audio signals.

In a specific embodiment, the EMT includes a stationary solenoid housing and a linearly vibrating solenoid (LVS) primarily vibrating along the Z-axis. Here, an X-Y-Z Cartesian coordinate system is adopted to facilitate illustration with its Z-axis generally parallel to the vaginal canal and pointing toward the uterus.

In a more specific embodiment, the LVS includes a permanent magnet core (PMC) in the shape of a rod oriented along the Z-axis, a coiled vibrating sleeve (CVS) enclosing the PMC, and a number of elastic anchoring wave traps (EAWT).

In a specific embodiment, the VTTH includes an inner vibration transmitting core shaped as a longitudinal rod along the Z-axis and having a proximal-end transmitting head coupling feature (THCF) shaped so as to allow a pre-application attachment and a post-application detachment between the VTTH and the vibration generator by the user. The VTTH also includes an outer tampon sheath, made of a sterile absorbent material, disposed in a surrounding relationship to the vibration transmitting core.

In a more specific embodiment, the outer surface of the vibration transmitting core or the outer tampon sheath has a number of surface protrusions so as to accentuate a corresponding VTTH vibration for increased effectiveness of easing the user's menstrual cramps.

In a more specific embodiment, the shape of the distal ends of both the inner vibration transmitting core and the outer tampon sheath are rounded for an increased user safety.

In another specific embodiment, the VTTH has an inner vibration transmitting core that has a rounded distal end, a proximal-end transmitting head coupling feature (THCF), and an intervening longitudinal spring along the Z-axis and attached to the rounded distal end. The THCF is shaped so as to allow a pre-application attachment and a post-application detachment between the VTTH and the vibration generator by the user. Additionally, an outer tampon sheath, made of a sterile absorbent material, is disposed in a surrounding relationship to the vibration transmitting core.

This summary is provided to introduce a selection of inventive concepts in a simplified form that will be further described below under the detailed description. As such, this summary is not intended to delimit the scope of the claimed subject matter.

These aspects of the present invention and their numerous embodiments are further made apparent, in the remainder of the present description, to those of ordinary skill in the art.

BRIEF DESCRIPTION OF THE DRAWINGS

In order to more fully describe numerous embodiments of the present invention, reference is made to the accompanying drawings. However, these drawings are not to be considered limitations in the scope of the invention, but are merely illustrative.

DETAILED DESCRIPTION OF PREFERRED EMBODIMENTS

The description above and below plus the drawings contained herein merely focus on one or more currently preferred embodiments of the present invention and also describe some exemplary optional features and/or alternative embodiments. The description and drawings are presented for the purpose of illustration and, as such, are not limitations of the present invention. Thus, those of ordinary skill in the art would readily recognize variations, modifications, and alternatives. Such variations, modifications and alternatives should be understood to be also within the scope of the present invention.

For a first purpose of maximizing relief from female user's menstrual cramps and maximizing female user's comfort, the present invention provides a tampon apparatus that is capable of electronically controlling the tampon vibration according to wide band variables. For a second purpose of reducing disposable cost, the present invention provides a tampon apparatus of which a vibrating tampon includes two portions: 1). a reusable vibration generator with wide band variable controls and a vibration member, and 2). a disposable VTTH. Unlike other traditional tampon construction, the present invention only requires the VTTH to be disposable instead of the whole vibrating tampon hence reducing its disposable cost.

Figure 1:
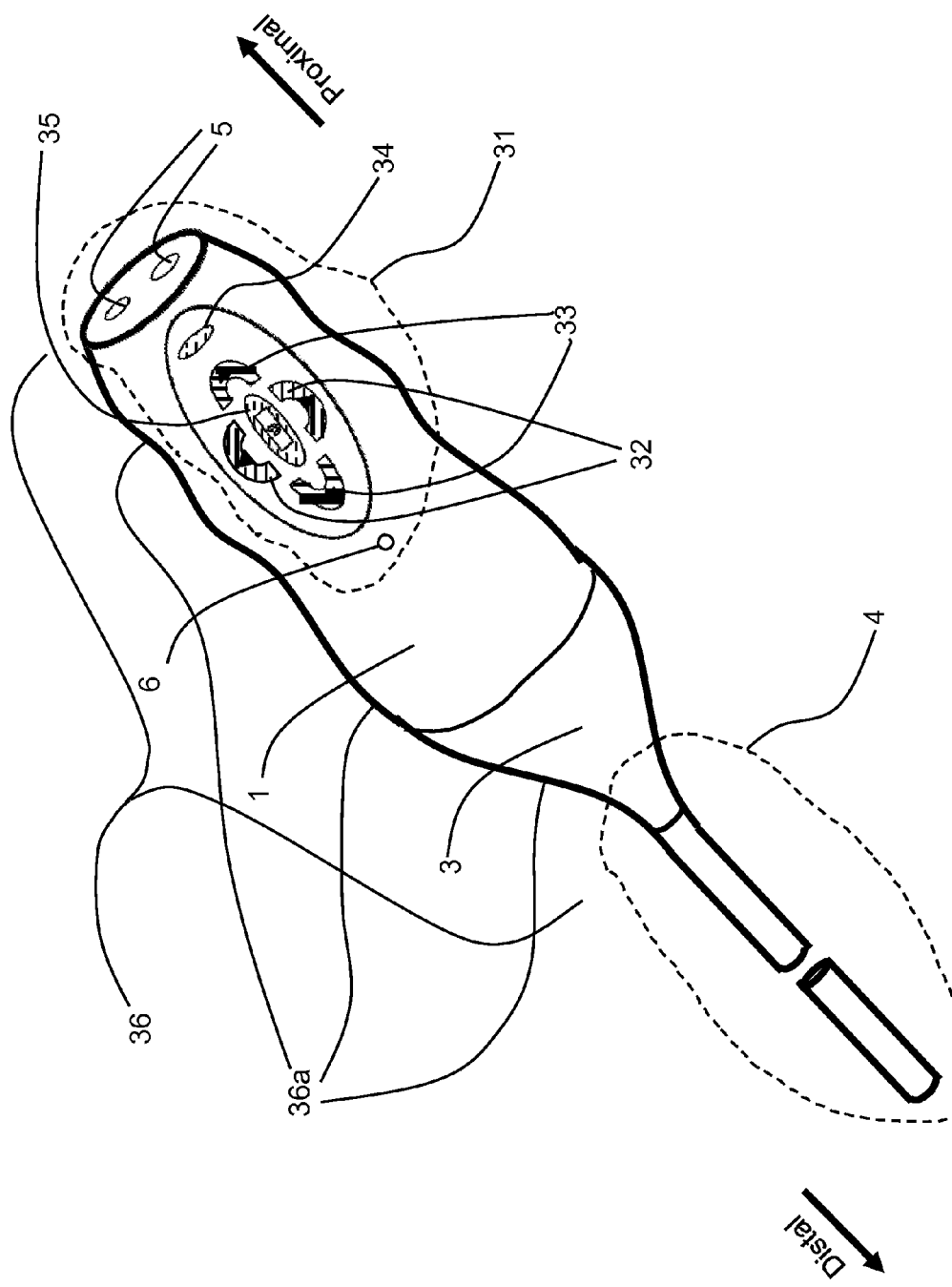
FIG. 1 is a perspective schematic illustration of an electronic remote control tampon under the present invention.

FIG. 1 is a perspective schematic of an electronic remote control tampon under the present invention, illustrating an ECWVT with low disposable cost. It includes an in-vitro vibration generator 36 that has a proximal end and a distal end. A mechanical vibration with controllable wide band variables is generated by the vibration generator 36 at its distal end. An in-vivo disposable VTTH 4, to be inserted to user's vaginal canal, is detachably coupled to the distal end of the vibration generator 36. The VTTH 4 transmits the variable wide band mechanical vibration from the vibration generator 36 into a corresponding tampon vibration acting upon the walls of a user's vaginal canal, thus easing a user's menstrual cramps with low disposable cost.

Figure 2:
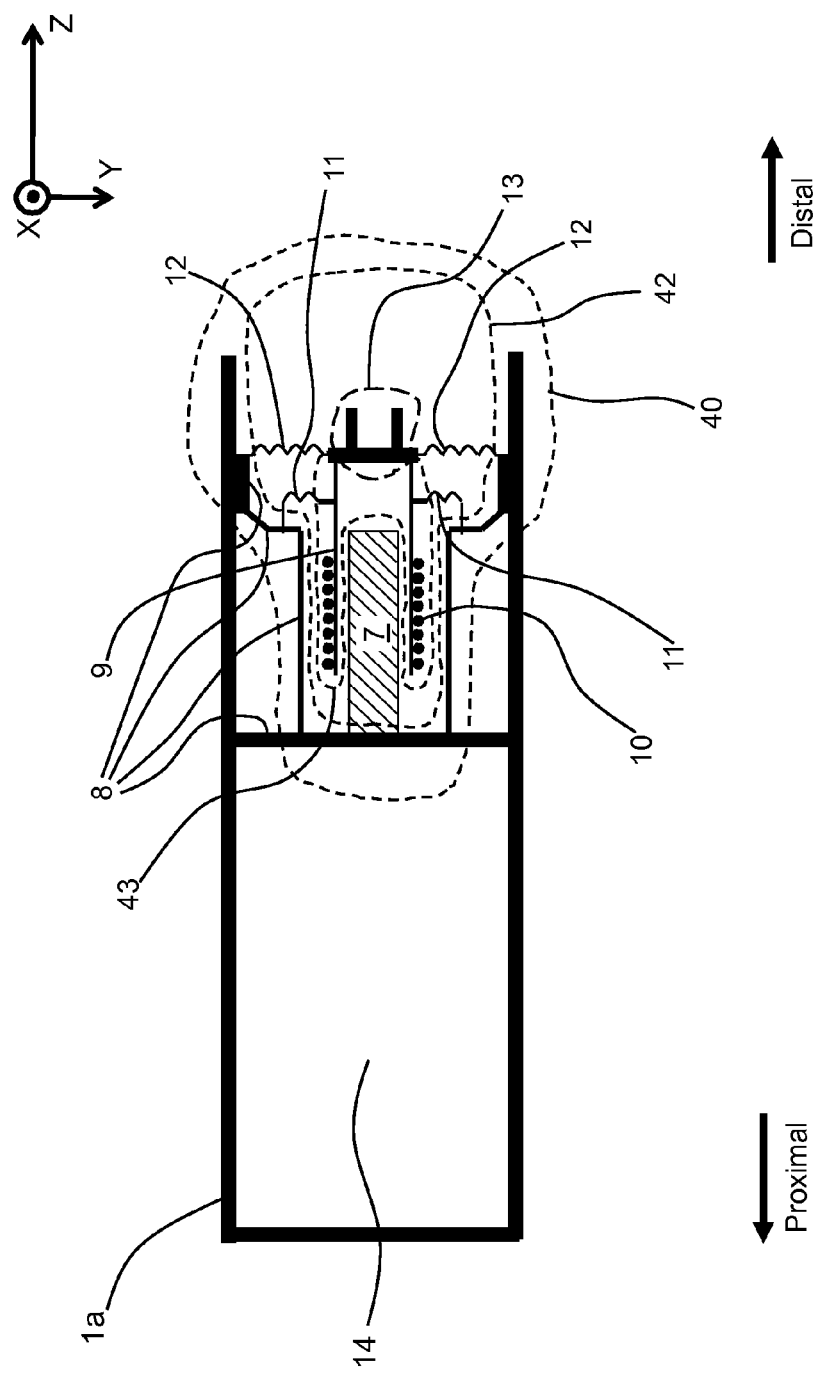
FIG. 2 is a cross sectional illustration of the internal structure of the electronic tampon remote controller chamber and an electromechanical transducer under the present invention.

FIG. 2 is a cross sectional illustration of the internal structure of the electronic tampon remote controller chamber and an electromechanical transducer under the present invention. With reference made to FIG. 1 and FIG. 2, the vibration generator 36 includes a remote electronic controller (REC) 1 located at the proximal side of the vibration generator (FIG. 1), an electromechanical transducer (EMT) 40 (FIG. 2) located inside an adapter 3 connecting REC 1 and VTTH 4, and a handled housing (HDH) 36a. The REC 1 functions to generate a variable wide band power electrical signal. The EMT 40 is electrically coupled to the REC 1 for generating a corresponding mechanical vibration upon being powered by a power electrical signal. The HDH 36a is for enclosing and affixing the REC 1 and the EMT 40.

The REC 1 has a user interface (UI) 31. While not visible here, the REC 1 also has a central signal generating (CSG) device, a power amplifier, and a power supply battery located inside a controller chamber 14. The CSG is coupled to the UI 31 for generating a wide band electrical signal according to user's control and operation via the UI 31. The power amplifier is coupled to the CSG for amplifying the wide band electrical signal into the power electrical signal for creating a mechanical vibration through the EMT 40.

The UI 31 includes a power on/off switch 34, a power on/off indicator light 6, vibration frequency adjustment buttons 32, wide band electrical signal source (e.g., acoustic variable, audio signal, white noise, pink noise, etc.) selection buttons 35, and wide band electrical signal power level (i.e., vibration magnitude) adjustment buttons 33.

The UI 31 also includes a set of external signal ports 5 for passing along numerous external electrical signal sources to become the wide band electrical signal upon their individual connection to a respective external electrical signal source selected via the selection buttons 35. As examples, the external electrical signal sources can be an audio signal, music signal, white noise, pink noise, or other color noises. As an alternative embodiment, some of the external signal ports 5 can instead be configured as a charging port for charging a rechargeable battery inside the vibration generator 36 following proper setting of the selection buttons 35.

As shown in FIG. 2, the EMC 40 has a stationary solenoid housing 1*a*. The EMC 40 also has a linearly vibrating solenoid (LVS) 42 located at the distal end. The EMC 40 is disposed inside and affixed to the solenoid housing 1*a*. The LVS 42 is capable of primarily vibrating along the Z-axis, where the Z-axis is oriented generally parallel to the user's vaginal canal and pointing toward the user's uterus. The corresponding X-Y-Z Cartesian coordinate system is also shown in FIG. 2.

The LVS 42 has a permanent magnet core (PMC) 7 located toward the distal-end of a coiled vibrating sleeve (CVS) 43, and numerous elastic anchoring wave traps (EAWT) 11 and 12 for supportively bridging the CVS 43 to the solenoid housing 1*a*. The PMC 7 is made in the shape of a rod oriented along the Z-axis. The CVS 43, enclosing the PMC 7, has a coil tube 9 surrounding the PMC 7 and a number of wrapped sleeve wound coils 10 wound around and along the coil tube 9 with its distal end attached to a female vibrating solenoid coupler (VSC) 13. The EAWT 11 and 12 are primarily oriented in the X-Y plane and they anchor the CVS 43 to the solenoid housing 1*a*. This allows a free travel of the CVS 43 primary along the Z-axis while limiting its travel range in the X-Y plane. Therefore, when a power electrical signal drives the sleeve wound coils 10 with a corresponding drive current, the LVS 42 generates a corresponding mechanical vibration at the VSC 13. The EMT 40 has a supporting shell 8 made of preferably highly magnetically permeable material to contain the magnetic field generated by the sleeve wound coils 10 inside. Located next to the proximal-end of the EMT 40 is a controller chamber 14 for hosting an electronic controller and power supply battery (not shown here to avoid excessive obscuring details). Thus, the electronic controller turns on/off the EMT 40 and controls its generated mechanical vibration according to the parametric settings of the UI 31 such as vibration signal waveform, frequency and power level.

Figure 3:
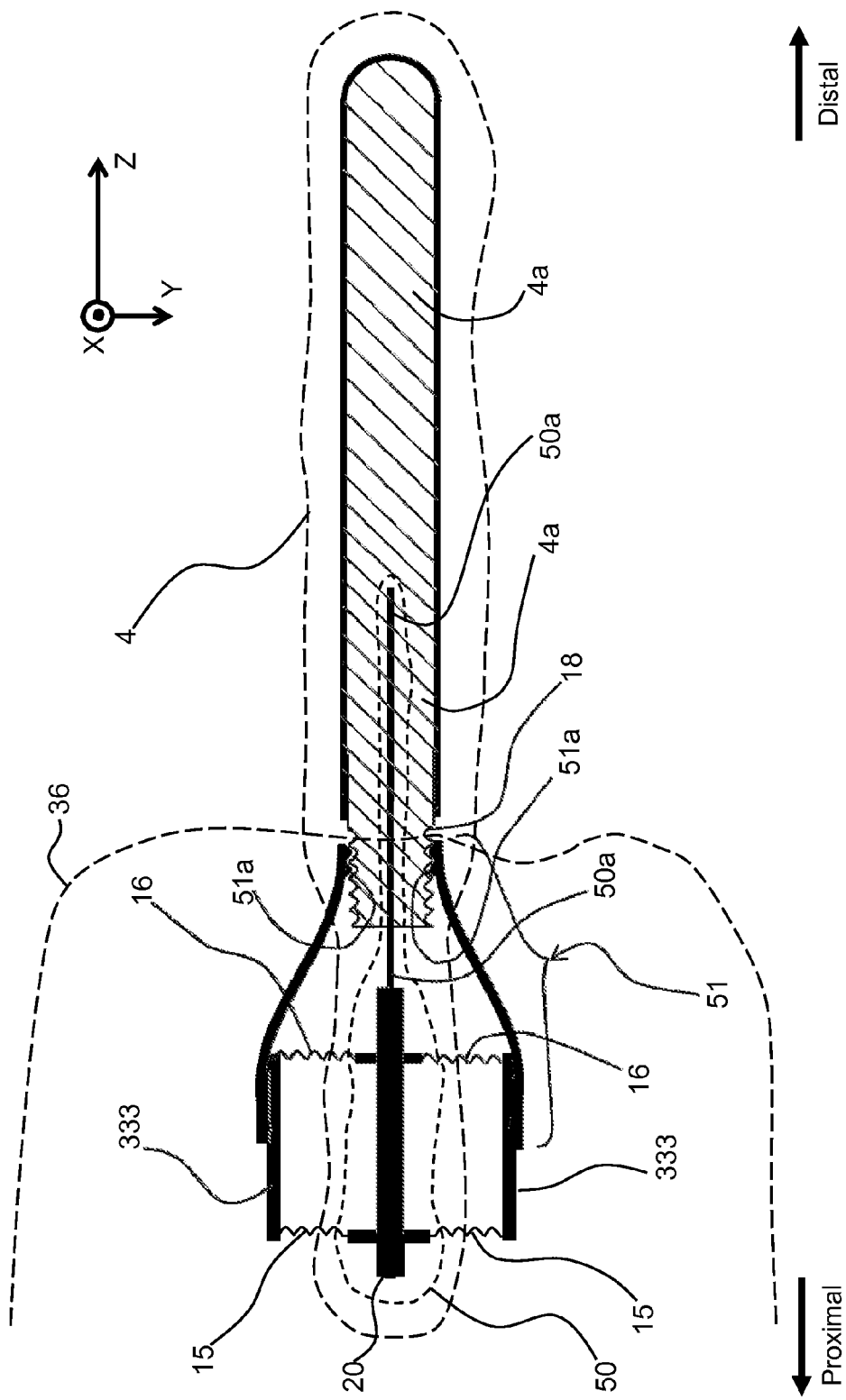
FIG. 3 is a cross sectional illustration of the internal structure of the vibrating tampon head.

FIG. 3 illustrates the cross-sectional view of the internal structure of the vibrating tampon head VTTH 4 together with the head adaptor as a part of the vibration generator 36 under the present invention. The VTTH 4 includes an inner vibration transmitting core 50. The vibration transmitting core 50 has a proximal male vibrating solenoid coupler (VSC) 20 and a distal vibrating rod core 50*a*. The distal vibrating rod core 50*a* has the shape of a longitudinal rod oriented along the Z-axis. Transmitting head coupling features (THCF) are provided on both the vibration generator 36 and the VTTH 4 and the THCFs are shaped and sized so as to allow a pre-application attachment and a post-application detachment between the VTTH 4 and the vibration generator 36 by the user. As an illustrative example, the THCF of the vibration generator 36 is an adapter shell screw feature 51*a* located on the inner surface of a tampon head adapter shell 51 of the vibration generator 36. Correspondingly, the THCF of the VTTH 4 is a tampon sheath screw feature 18 located on the outer surface of a distal vibrating tampon sheath 4*a* of the VTTH 4. As a side remark, the proximal end of the tampon head adapter shell 51 is bonded to the distal end of a root support shell 333 that is part of the solenoid housing 1*a* (see FIG. 2). The distal vibrating tampon sheath 4*a* is made of a sterile absorbent material and is disposed in a surrounding relationship to the vibration transmitting core 50. Other examples of THCF include various snap on/off mechanisms and latch on/off mechanisms.

Figure 4:
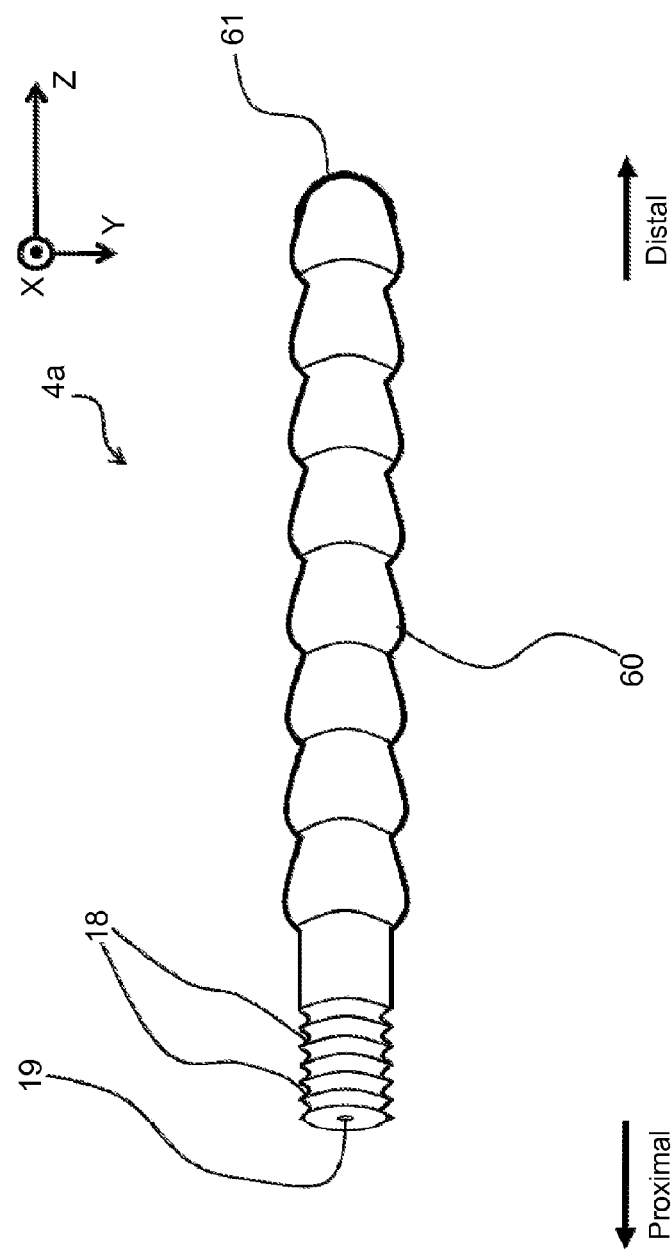
FIG. 4 is a perspective illustration of the shape of a vibrating tampon head under the present invention.
Figure 5:
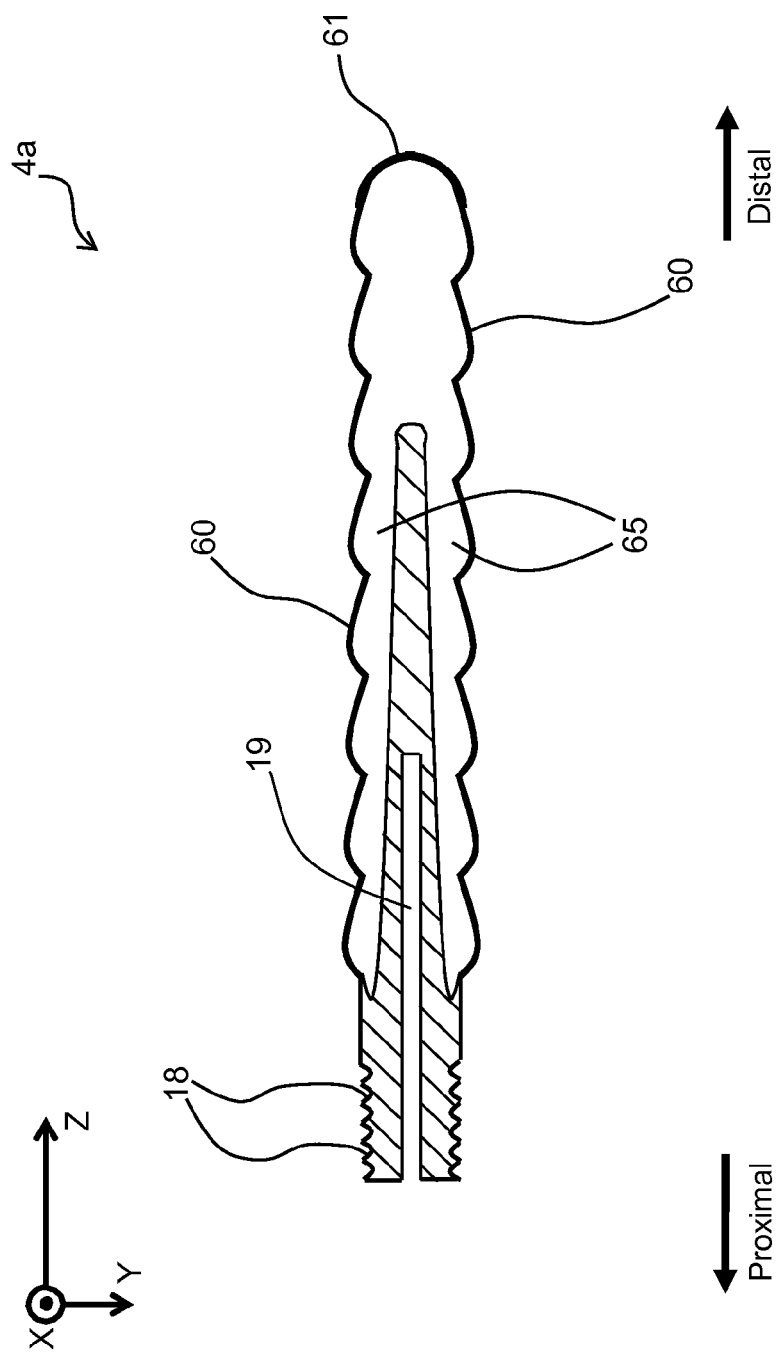
FIG. 5 is a cross sectional illustration of an internal structure of a vibrating tampon head under the preset invention.

FIG. 4 is a perspective illustration of the shape of a vibrating tampon head under the present invention. FIG. 5 illustrates a cross sectional view of an internal structure of a vibrating tampon head under the preset invention. Within the VTTH 4 of FIG. 3, the outer surface of either the distal vibrating rod core 50*a* or the distal vibrating tampon sheath 4*a* can have a number of surface protrusions 60 and a rounded distal end 61, as illustrated in FIG. 4 and FIG. 5, so as to accentuate a corresponding vibration of the VTTH 4 for increased effectiveness of easing the user's menstrual cramps.

Further in FIG. 3, the tampon head adapter shell 51 together with the adapter shell screw feature 51*a* supports the THCF. The adapter shell screw feature 51*a* engages and fits the tampon sheath screw feature 18 (shown in FIG. 3 and FIG. 4). The vibration transmitting core 50 is supported by the rubber wave trap 15 and the supporting wave trap 16. In turn, the rubber wave trap 15 and the supporting wave trap 16 are supported by the root support shell 333. The proximal end of the vibration transmitting core 50 has the male vibrating solenoid coupler VSC 20. The male vibrating solenoid coupler VSC 20 of FIG. 3 is coupled to the female vibrating solenoid coupler VSC 13 of FIG. 2.

Further in FIG. 4, the hole at the proximal end shows the proximal end of the base tube 19 of the distal vibrating tampon sheath 4*a* whereas the screw tracks near the proximal end illustrate the tampon sheath screw feature 18.

The internal structure of the distal vibrating tampon sheath 4*a* of FIG. 4 is illustrated in FIG. 5. The distal vibrating tampon sheath 4*a* has a rubber supporting screw stick having the tampon sheath screw feature 18 and the base tube 19 for connection to the distal vibrating rod core 50*a* of FIG. 3. The distal vibrating tampon sheath 4*a* includes fibrous or absorbent material 65.

Figure 6:
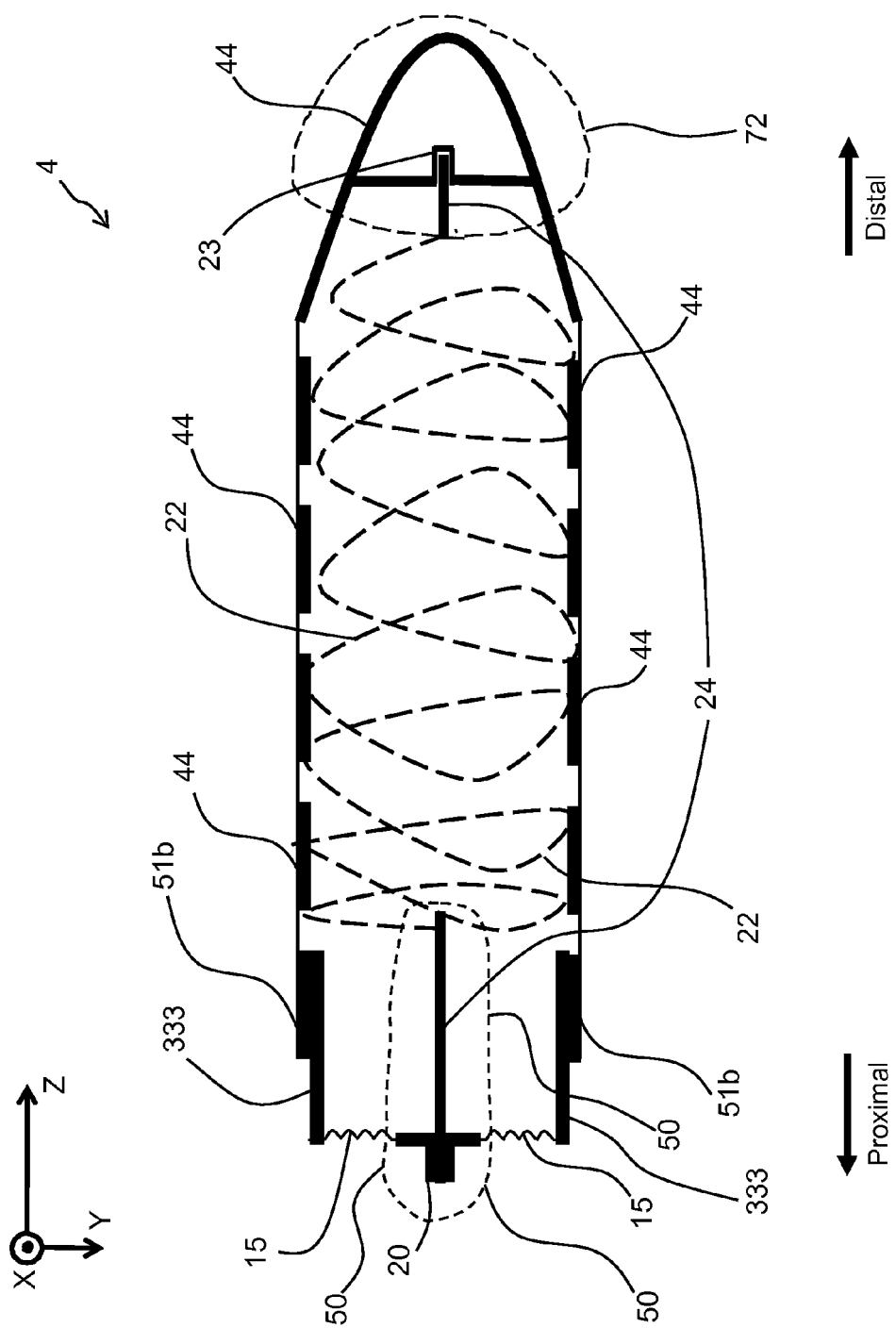
FIG. 6 is a cross sectional illustration of another internal structure of a vibrating tampon head but without head adaptor.

FIG. 6 illustrates the cross sectional view of an internal structure of the vibrating transmitting tampon head VTTH 4 in the absence of a head adaptor under the present invention. The VTTH 4 has numerous direct vibrating soft tampon segments 44, a rounded distal end 72, a vibrating body spring 22 for enhancing mechanical vibration, a vibration transmitting core 50 supported by the rubber trap 15 with the rubber trap 15 in turn supported by the root support shell 333. A transmitting head coupling feature (THCF) 51*b* engages and connects the root support shell 333 and the direct vibrating soft tampon segments 44. The vibration transmitting core 50 has a distal-end vibration transmitting core 24 and a proximal-end male vibrating solenoid coupler VSC 20 destined for connection to the female solenoid coupler VSC 13 of FIG. 2. The distal-end vibration transmitting core 24 is inserted into a distal tube 23 for transmitting vibration to the rounded distal end 72.

Under the present invention, within the VTTH 4 in all figures, the distal ends of both the vibration transmitting core 50 and the distal vibrating tampon sheath 4a are rounded for user safety and the illustration includes:

a rounded distal end 61 in FIG. 4;

the proximal-end transmitting head coupling feature (THCF) 51b;

an intervening longitudinal spring oriented along the Z-axis (FIG. 6) and attached to the rounded distal end with the THCF 51b shaped so as to allow a pre-application attachment and a post-application detachment between the VTTH 4 and the vibration generator 36 by the user; and the distal vibrating tampon sheath 4a made of a sterile absorbent material 65 as shown in FIG. 4 and FIG. 5. In addition, the distal vibrating tampon sheath 4a is disposed in a surrounding relationship to the distal vibrating rod core 50a as shown in FIG. 3.

Figure 7:
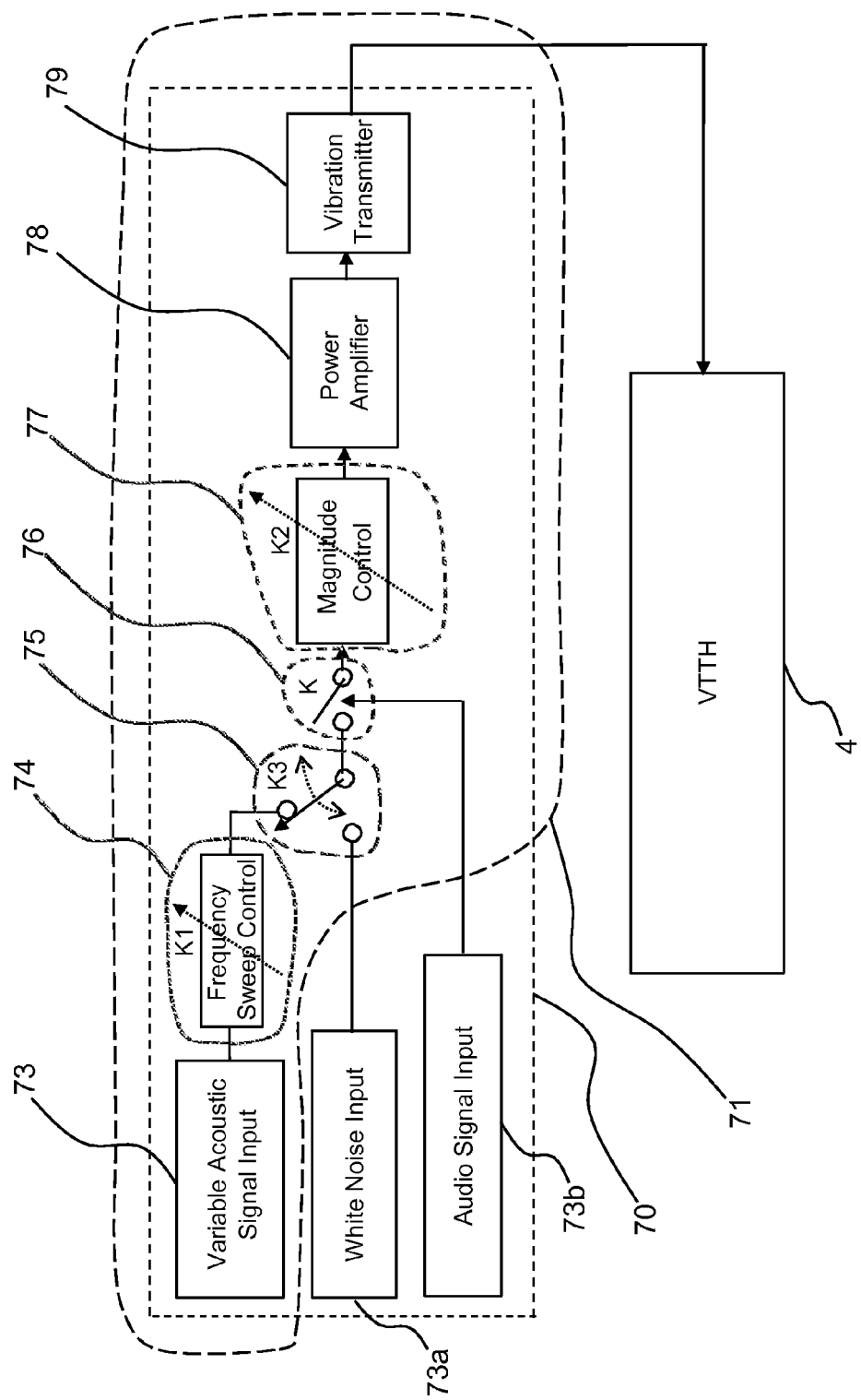
FIG. 7 is a block diagram illustration of the electronic wide band variable vibrating tampon system under the present invention.

FIG. 7 is a block diagram illustration of the electronic wide band variable vibrating tampon system under the present invention. As shown in FIG. 7, a vibration generation subsystem 70 has a wide variable band controller plus multiple selectable inputs. This vibration generation subsystem 70 includes a vibration generator 71 having a wide variable band controller operatively coupling with the multiple selectable inputs and the VTTH 4. The vibration generator 71 includes an electromechanical transducer aka Vibration Transmitter 79 powered by a Power Amplifier 78 in turn driven by an electrical signal Magnitude Control K2 77. The input of the Magnitude Control K2 77 is selected by a signal switch K 76 to select from the output of switch K3 75 or from an Audio Signal input 73b. The switch K3 75 selects a signal between the output of the Frequency Sweep Control K1 74 and a Color Noise Input such as a White Noise Input 73a. In parallel, the Frequency Sweep Control K1 74 adjusts the signal frequency generated from a Variable Acoustic Signal Input 73. Thus the mechanical vibration transmitted to the VTTH 4 is widely selectable, adjustable, and controllable for a user to customize and to maximize the relief from the feminine menstrual cramps or to maximize the user's comfort.

Figure 8:
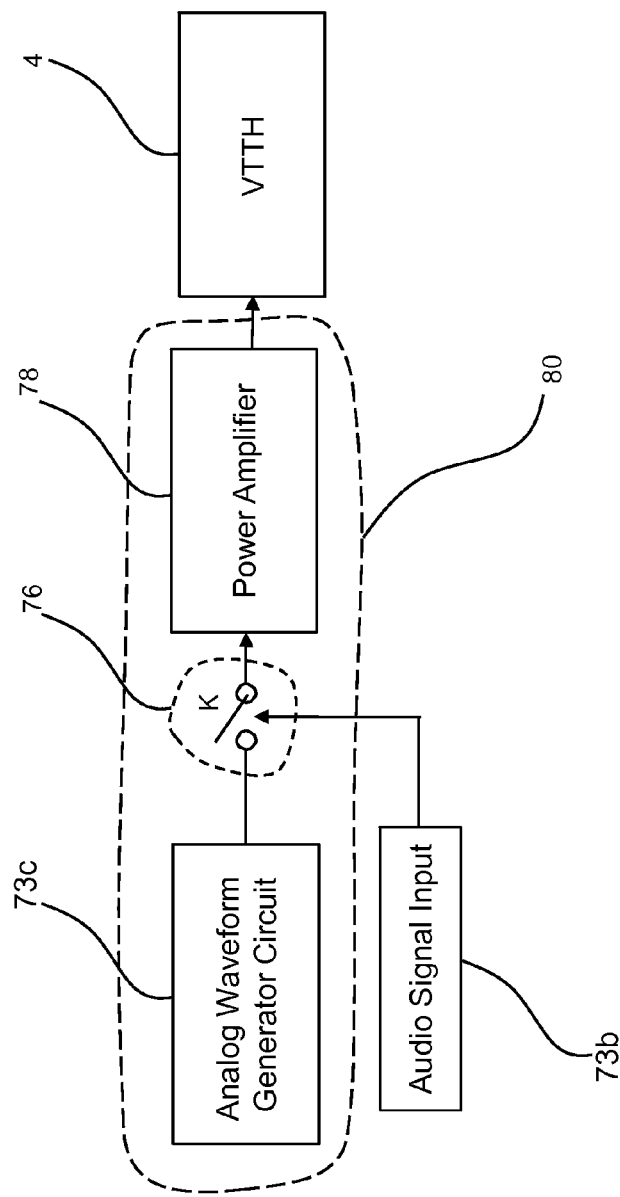
FIG. 8 is a block diagram illustration of an analog implementation of the electronic wide band variable vibrating tampon system under the present invention.

FIG. 8 is a block diagram illustration of an analog implementation of the electronic wide band variable vibrating tampon system under the present invention. The analog implementation includes a VTTH 4, a vibration generator 80, and an Audio Signal Input 73b. The vibration generator 80 includes a Power Amplifier 78, a signal switch K 76 and an Analog Waveform Generator Circuit 73c.

Figure 9:
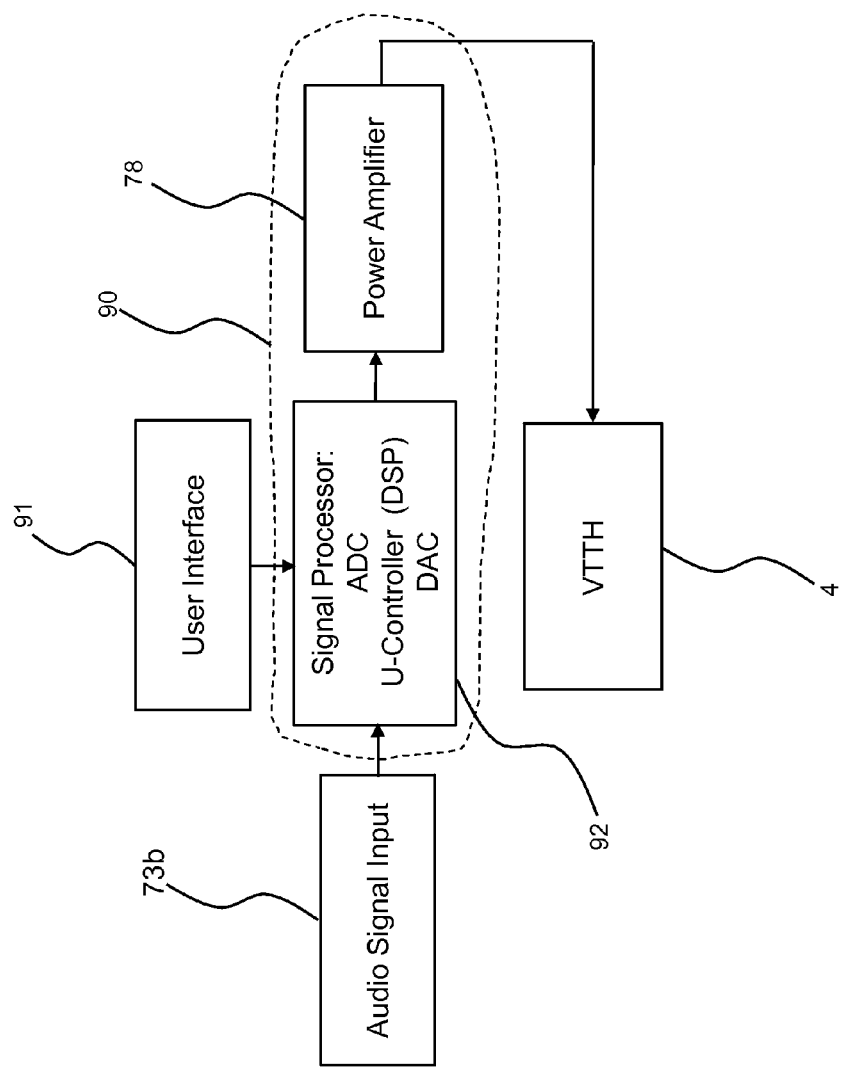
FIG. 9 is a block diagram illustration of a digital software implementation of the electronic wide band variable vibrating tampon system under the present invention.

FIG. 9 is a block diagram illustration of a digital software implementation of the electronic wide band variable vibrating tampon system under the present invention. In FIG. 9, the VTTH 4 is driven by the vibration transmitted from a vibration generator 90 under the control of its embedded digital software. The vibration generator 90 includes a Power Amplifier 78 and a Signal Processor 92. The Signal Processor 92 receives an audio Signal Input 73b. Being controlled by a user, the User Interface 91 in turn adjusts the operation of the Signal Processor 92. Among other attributes, the Signal Processor 92 includes an analog to digital signal converter (ADC), a digital signal processor (DSP), and a digital to analog converter (DAC). The audio signal input 73b can be either an analog audio signal or a digital audio signal. If it is an analog audio signal, via an analog audio cable the ADC within the signal processor 92 receives it and converts it into a digital audio signal and then the digital signal processor within the signal processor 92 processes it. The processed digital signal is then converted into its analog form to drive the power amplifier 78. On the other hand, if the audio signal input 73b is a digital audio signal, either in a compressed digital audio form such as the MP3 or in an uncompressed digital audio form, via a digital communication cable or bus such as the Universal Serial Bus (USB), the digital audio signal is transmitted directly to the DSP of the signal processor 92 without going through the ADC. To those skilled in the art, therefore, the vibration variables of the VTTH 4 are controlled by the vibration generator 90 through the Signal Processor 92. Either in analog form or in digital form, examples of an audio signal input includes a music signal and a simple sound signal such as white noise, pink noise, red noise, and grey noise but in an electronic form.

Figure 10:
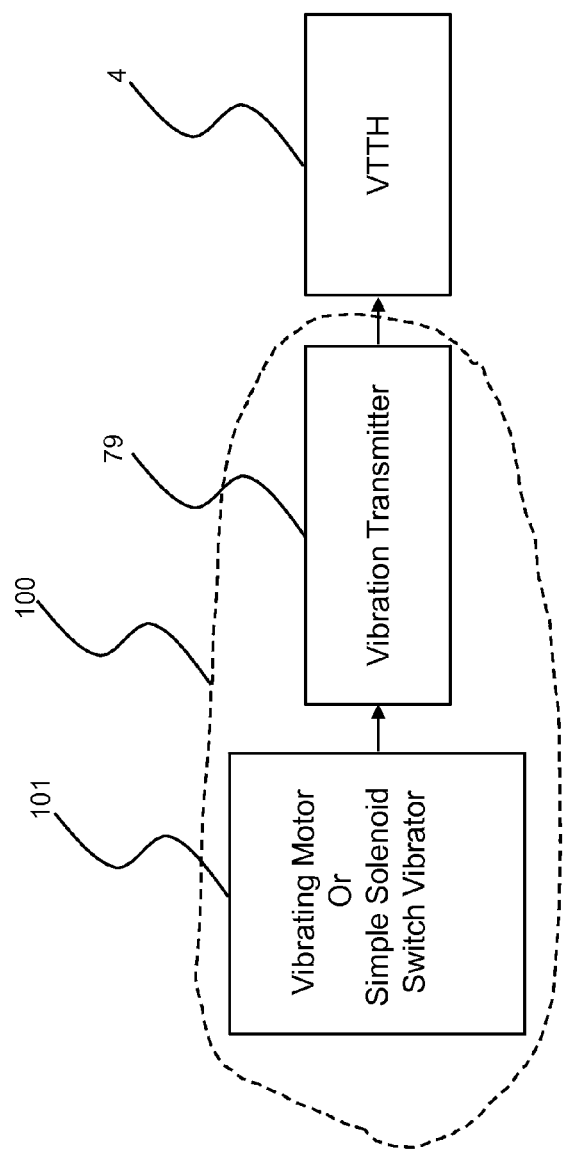
FIG. 10 is a block diagram illustration of an electromechanical hardware implementation of the electronic wide band variable vibrating tampon system under the present invention.
Figure 11:
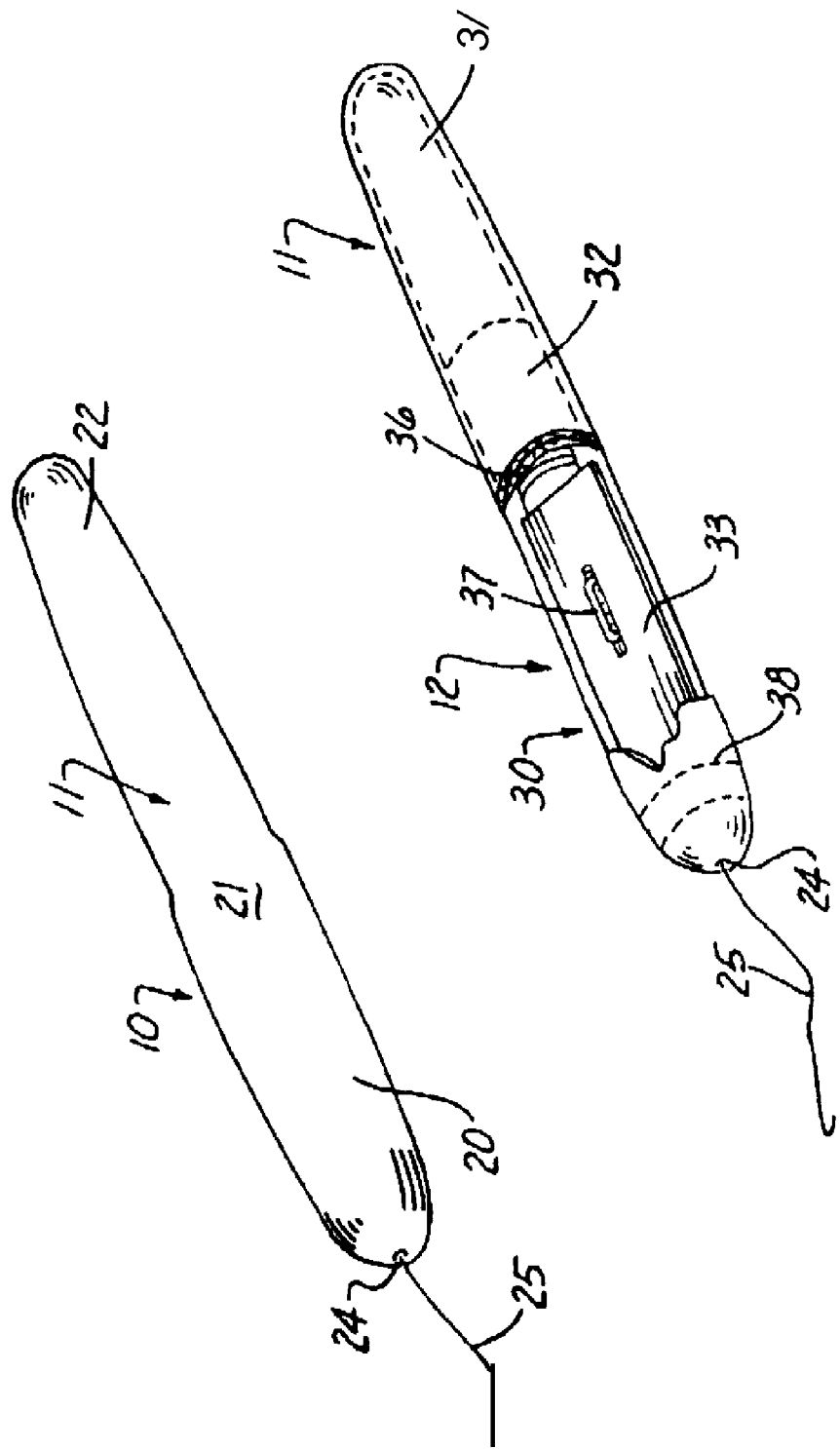
FIG. 11 is a perspective schematic illustration of a prior art vibrating tampon disclosed in U.S. Pat. No. 5,782,779 by Kilgore.
Figure 12:
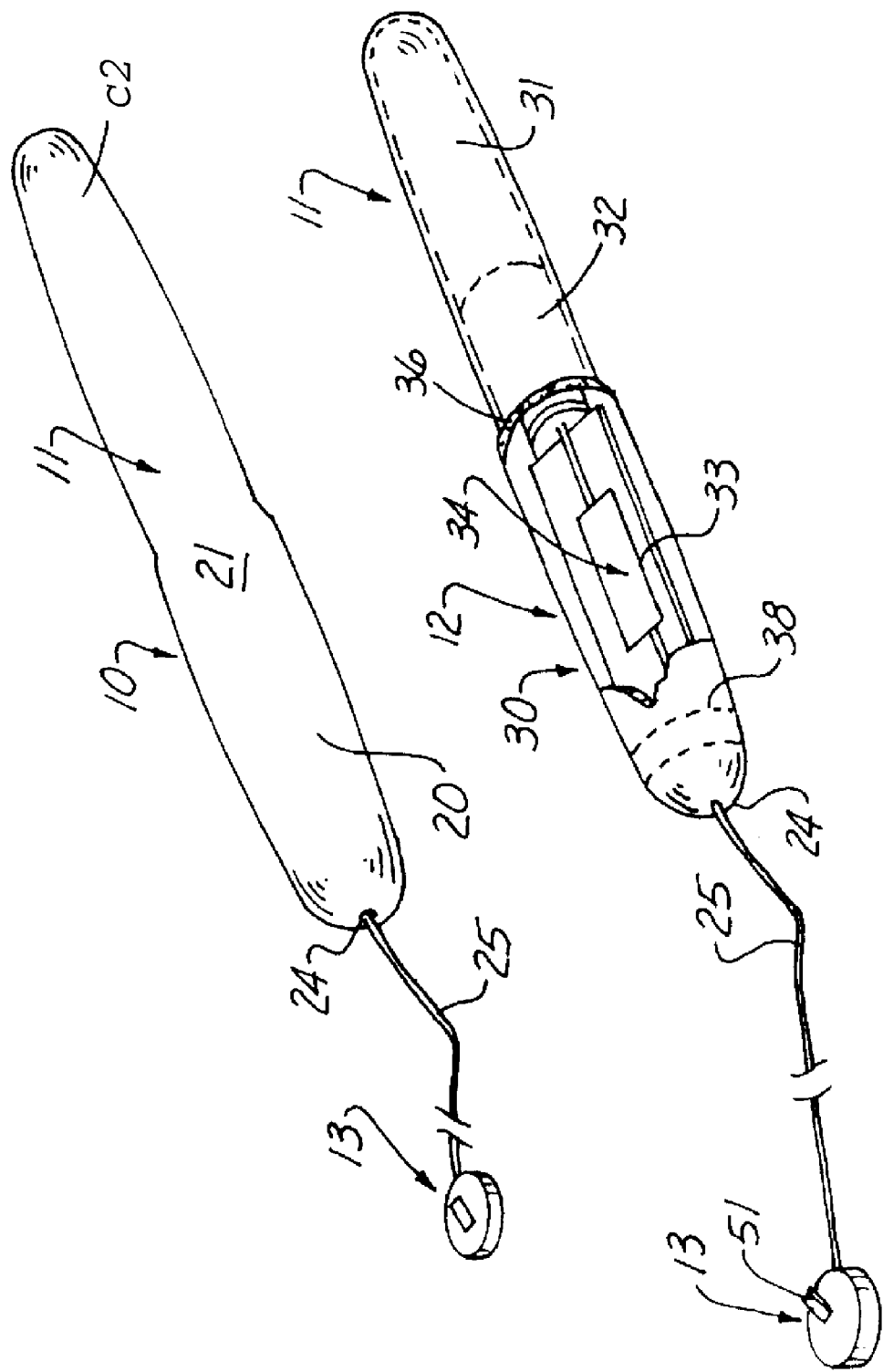
FIG. 12 is a perspective schematic illustration of a prior art improved vibrating tampon disclosed in U.S. Pat. No. 6,183,428 by Kilgore.
Figure 13:
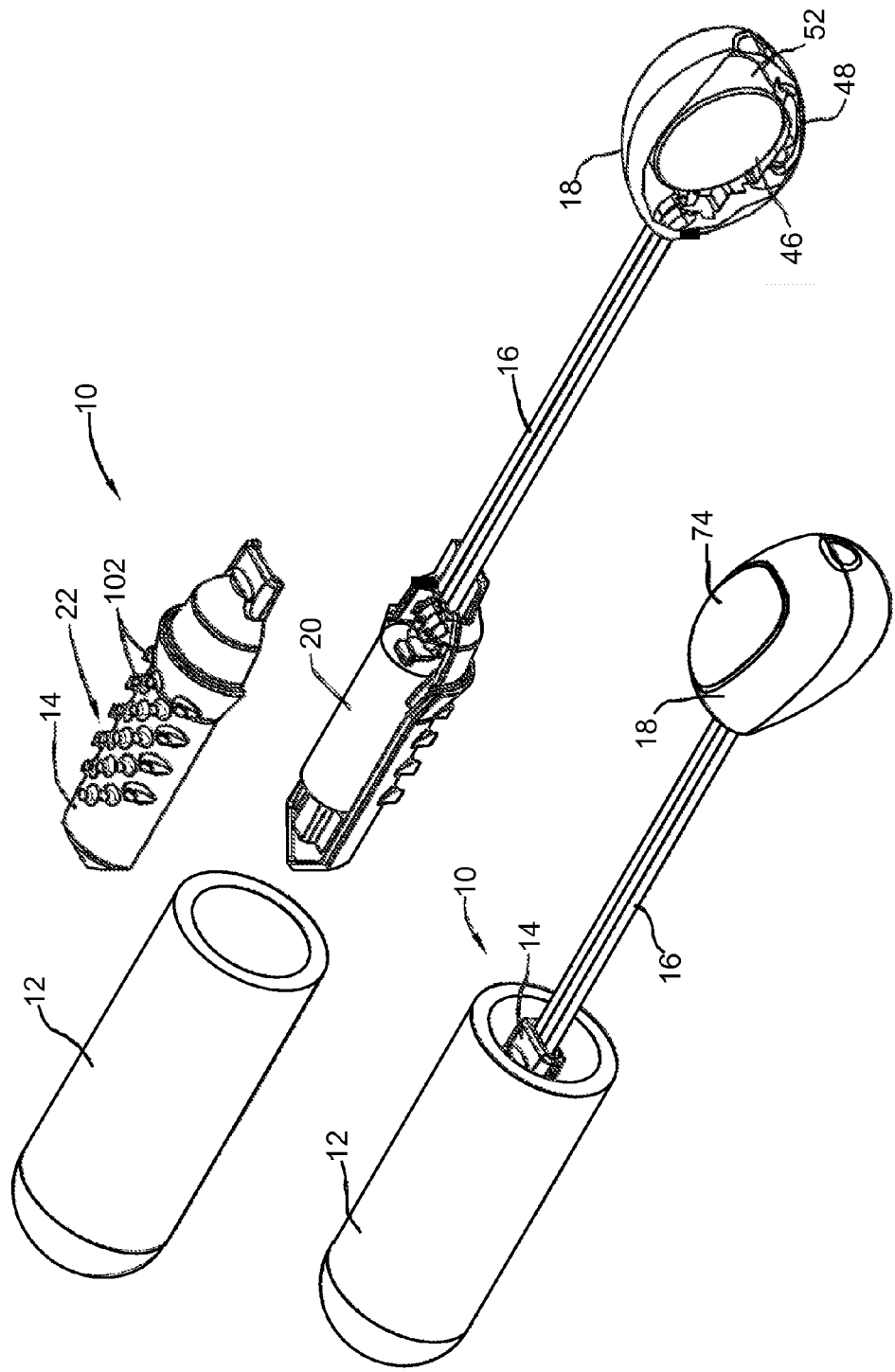
FIG. 13 is a perspective schematic illustration of a prior art of another improved vibrating tampon disclosed in US patent application publication No.: US 2007/0260210 A1 by Conroy.

FIG. 10 illustrates, with a block diagram, an electromechanical hardware implementation of the electronic wide band variable vibrating tampon system under the present invention. The VTTH 4 is driven by vibration from a vibration generator 100 having a vibrating motor or a simple solenoid switch vibrator 101. The vibration generator 100 also has a vibration transmitter 79 for transmitting vibration to the VTTH 4.

Throughout the description and drawings, numerous exemplary embodiments were given with reference to specific configurations. It will be appreciated by those of ordinary skill in the art that the present invention can be embodied in numerous other specific forms and those of ordinary skill in the art would be able to practice such other embodiments without undue experimentation. The scope of the present invention, for the purpose of the present patent document, is hence not limited merely to the specific exemplary embodiments of the foregoing description, but rather is indicated by the following claims. Any and all modifications that come within the meaning and range of equivalents within the claims are intended to be considered as being embraced within the spirit and scope of the present invention.

We claim:

1. An electronically controlled wide band vibrating tampon (ECWVT) with low disposable cost, the ECWVT comprising:

an electronically controlled in vitro vibration generating means, having a proximal end and a distal end, for generating a variable wide band mechanical vibration at the distal end; and a disposable in vivo vibration transmitting tampon head (VTTH) detachably coupled to the distal end, for transmitting the variable wide band mechanical vibration into a corresponding tampon vibration upon the wall of a user's vaginal canal whereby easing a user's menstrual cramps with low disposable cost; wherein the vibration generating means further comprising:

a proximal end remote electronic controller (REC) for generating a variable wide band power electrical signal;

a distal end electromechanical transducer (EMT) electrically coupled to the REC for, upon being powered by the power electrical signal, generating a corresponding mechanical vibration; and a handled housing (HDH) for enclosing and affixing the REC and the EMT therein; and wherein the EMT comprising, expressed in an X-Y-Z Cartesian coordinate system with the Z-axis generally parallel to the vaginal canal and pointing toward the uterus:

a stationary solenoid housing; and a linearly vibrating solenoid (LVS), disposed inside and affixed to the solenoid housing, having a distal-end vibrating solenoid coupler (VSC) primarily vibrating along the Z-axis; and wherein the LVS further comprising:

a proximal-end permanent magnet core (PMC) in the shape of a rod oriented along the Z-axis;

a coiled vibrating sleeve (CVS), enclosing the PMC, having a number of sleeve coils wrapped thereon and with its distal end attached to the VSC; and a plurality of elastic anchoring wave traps (EAWT), primarily oriented in the X-Y plane, anchoring the CVS to the stationary solenoid housing for allowing a free CVS travel along the Z-axis while limiting its travel in the X-Y plane whereby, upon powering the sleeve coils with a drive current corresponding to the power electrical signal, the LVS generates a corresponding mechanical vibration at the VSC.

\* \* \* \* \*